United States Patent

Duhamel et al.

[11] Patent Number: 5,208,255
[45] Date of Patent: May 4, 1993

[54] THIOESTER ENANTIOMERIC COMPOUNDS AND THEIR THERAPEUTIC USES

[75] Inventors: Pierre Duhamel; Lucette Duhamel, both of Mont Saint Aignan; Denis Danvy, Cany Barville; Jean-Christophe Plaquevent, Notre Dame De Bondeville; Bruno Giros, Kremlin Bicetre; Claude Gros, Paris; Jean-Charles Schwartz, Paris; Jeanne-Marie Lecomte, Paris, all of France

[73] Assignee: Societe Civile Bioprojet, Paris, France

[21] Appl. No.: 274,884

[22] Filed: Nov. 22, 1988

[30] Foreign Application Priority Data

Nov. 24, 1987 [FR] France ............................ 87 16239

[51] Int. Cl.$^5$ ............................................. A61K 31/21
[52] U.S. Cl. .................................... 514/513; 558/254
[58] Field of Search ........................ 558/254; 514/513

[56] References Cited

U.S. PATENT DOCUMENTS

| 4,513,009 | 4/1985 | Roques et al. | 558/254 |
| 4,740,499 | 4/1988 | Olins | 558/254 |
| 4,798,904 | 1/1989 | Delaney et al. | 558/254 |

Primary Examiner—Mary C. Lee
Assistant Examiner—Joseph K. McKane
Attorney, Agent, or Firm—Larson and Taylor

[57] ABSTRACT

The (R) or (S) isomer of acetorphan or N-/2-acetylthiomethyl)-1-oxo-3-phenylpropyl/(S) alanine methyl ester is prepared by splitting of racemic acetylthio-2-benzylpropanoic acid by reaction with ephedrin, separation of the enantiomeric salt obtained, then freeing of the acid and coupling with the corresponding amino acid ester. The obtained preparations possess remarkable therapeutic activities and can notably be used as drugs.

6 Claims, No Drawings

THIOESTER ENANTIOMERIC COMPOUNDS AND THEIR THERAPEUTIC USES

This invention relates to new amino acid-derived enantiomeric compounds, a process for their preparation and their therapeutical use.

The compound N-/2-mercaptomethyl-1-oxo-3-phenyl propyl/-glycine or thiorphan has been described under its (R,S) racemic form as a powerful inhibitor of enkephalinase, an enzyme which is responsible for the inactivation of enkephalins, and as a less powerful inhibitor of angiotensin conversion enzyme or ACE (Roques et al. Nature, 1980, 288, 286, Roques et al. EP-A-0038758; US-A-4513009). This compound when used intravenously or intracerebroventricularly has analgesic properties which are linked to the protection of endogenous enkephalins but also, at a higher dose, a cardiovascular activity which may either entail a number of disadvantages or be desirable according to therapeutic applications. The same properties and potential disadvantages may be found in one of its derivatives, Acetorphan or (R,S) N-/2-acetylthiomethyl-1-oxo-3-phenyl propyl/-glycine benzyl ester, which however has the advantage of being active intravenously, at a small dose (around 1 mg/kg) whereas (R,S) thiorphan is only active intracerebrally or in about 50 times higher doses, systemically (Lecomte et al., J. Pharmacol. Exp. Ther., 1986, 237, 937).

An asymetrical synthesis process, hardly applicable to technical preparation, has recently allowed one to obtain separately the two enantiomers of thiorphan (Evans et al., J. Org. Chem. 1985, 50, 1830) and to show that, whereas these two compounds have an inhibiting activity towards neighbouring enkephalinase, ACE's inhibiting activity was almost exclusively attributable to the (S) isomer, and its analgesic (intracerebral) activity principally to the (R) isomer. Moreover the equiactivity towards enkephalinase of the two isomers of thiorphan, also obtained by a separation procedure hardly applicable to technical preparation, has been confirmed (FourniéZaluski et al., J. Med. Chem. 1986, 29, 751).

The aim of this invention is

1. To supply, as new industrial products, essentially pure preparations of (R) and (S) isomers of Acetorphan and like derivatives,
2. To contribute a new separation process, applicable to the technical preparation of (R) and (S) isomers of Acetorphan and like derivatives,
3. To describe analgesic activities observed after oral administration of a high dose and without negative side effects linked to ACE inhibition,
4. To describe a number of other effects of these compounds on the alimentary canal, which effects allow original therapeutic activities in a number of functional diseases such as 'irritable colon', for which no effective treatment has yet been suggested, as well as a protective effect for the natriuretic auricular factor, which allows one to undertake an original therapeutic activity in the cardiovascular and renal fields such as cardiac insufficiency, high blood pressure and hepatorenal insufficiency,
5. To provide new drugs by the therapeutic use of these compounds.

The inventive compounds have the following formula:

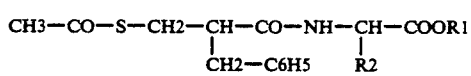

(R) and (S)

in which

R1 = CH3 or CH2—C6H5 and R2 = H or CH3

The above-defined compounds are the following:

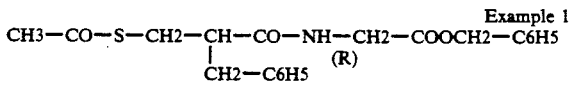
Example 1

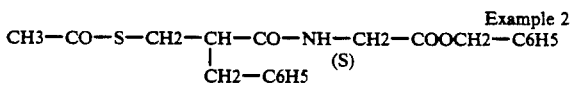
Example 2

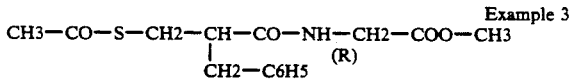
Example 3

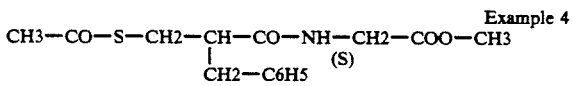
Example 4

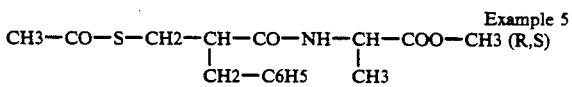
Example 5

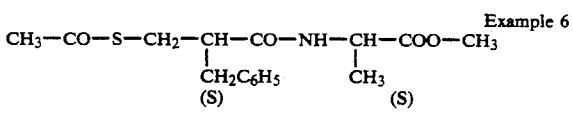
Example 6

The inventive compounds are prepared by the following reaction scheme:

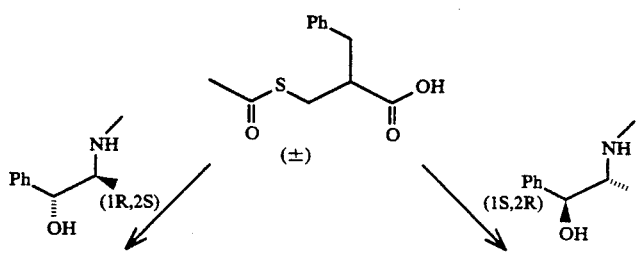

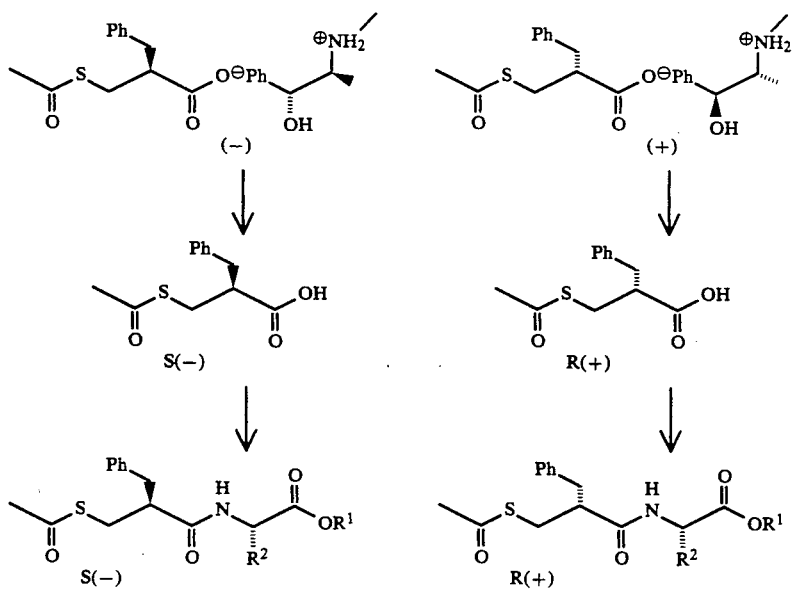

Ex. 1: R1 = CH2Ph R2 = H
Ex. 2: R1 = CH2Ph R2 = H
Ex. 3: R1 = CH3 R2 = H
Ex. 4: R1 = CH3 R2 = H
Ex. 5: R1 = CH3 R2 = CH3
Ex. 6: R1 = CH3 R2 = CH3

The initial step is the splitting of 3-acetylthio2-benzylpropanoic acid. To this end the racemic acid is preferably reacted with ephedrin (+), or (−) especially in ether. The obtained salt is recrystallized for example in a mixture of dichloromethane/petroleum ether. The obtained salts are optically pure. The acid is liberated by the action of, for instance, hydrochloric acid and the coupling with the corresponding amino acid ester (glycine or alanine) is done preferably in the presence of dicyclohexylcarbodiimide (DCC) for coupling agent, and hydroxybenzotriazole (HOBT) to avoid racemisation.

EXAMPLE 1

N-/2-acetylthiomethyl-1-oxo-3-phenyl propyl/-glycine (R) benzyl ester. Synthesis of ephedrinium (+) 3-acetylthio-2-benzylpropionate.

In an erlenmeyer flask 10 g (42 mmol) racemic acetylthio-3-benzyl-2-propanoic acid are introduced. This is dissolved in 50 ml ether, then 3.47 g (+)ephedrin (21 mmol) are added. This is stirred until dissolution and left to crystallize at room temperature. The first crystals appear after a few hours (3 hrs). After leaving the salt 3 days at room temperature it is filtrated. The salt is ground and washed with 5 ml ether.

(+) salt mass obtained: 4.2 g-Yield 49% F=103°-114° C. (Microscope). $(\alpha)_D^{25} = +43.0°$ (c=1.20 in MeOH)

4.1 g salt ($(\alpha)_D^{25} = +43.0°$) are dissolved in 20 ml hot dichloromethane. After cooling down to room temperature 20 ml petroleum ether are added. This is left to crystallize at room temperature.

It is filtrated after 33 hours.

(+) salt mass obtained: 2.80 g-Yield 68% F=115°-123° C. (Microscope) $(\alpha)_D^{25} = +47.5°$ (c=1.20 in MeOH)

The above step is repeated by dissolving 2.39 g salt ($(\alpha)_D^{25} = -47.5°$) in 11 ml hot CH2Cl2 and 7 ml petroleum ether. This is left to crystallize for 23 hours and filtrated.

Salt mass obtained: 1.69 g-Yield 71%. Yield of the 2 recrystallizations: 48%. F=122°-124° C. (Microscope) $(\alpha)_D^{25} = +49.2°$ (c=1.20 in MeOH).

Synthesis of R (+) 3-acetylthio-2-benzylpropanoic acid.

1.6 g of the above salt (+) ($(\alpha)_D^{25} = +49.2°$) are dissolved in a mixture of 20 ml water and 15 ml CH2Cl2. 1N hydrochloric acid is added until pH=1. The organic phase is separated and the aqueous phase is extracted with 15 ml CH2Cl2. The organic phases are combined, dried upon MgSO4 and concentrated to give (+) 3-acetylthio-2-benzylpropanoic acid.

(+) acid mass obtained: 0.95 g-Yield 97%. $(\alpha)_D^{25} = +35.3°$ (c=1.30 in MeOH).

In a three-necked flask with calcium chloride guard and magnetic stirrer is placed 3.74 g R(+) acid (15.7 mmol, $(\alpha)_D^{25} = +35.4°$) dissolved in 26 ml anhydrous THF. At around 0°-5° C. are added in sequence 5.29 g benzyl glycinate (in the form of paratoluene sulfonate, 15.7 mmol) and 1.58 g triethylamine (15.7 mmol) in 30 ml chloroform, 2.40 g hydroxybenzotriazole (HOBT) (15.7 mmol) in 22 ml THF and 3.24 g dicyclohexylcarbodiimide (DCC) (15.7 mmol) in 19 ml chloroform. This is left to warm up to 20° C. after which it is shaken during 5 hours.

The dicyclohexylurea (DCU) is filtrated and evaporated to dryness. The yellow residue is absorbed with 40 ml ethyl acetate. The DCU which has again precipitated is filtrated. The organic phase is sequentially washed with 1×20 ml water, 3×20 ml saturated sodium hydrogen carbonate solution, 1×20 ml water and 1×20 ml saturated sodium chloride solution. This is dried upon magnesium sulfate and evaporated to dryness. A yellow solid residue is obtained. It is dissolved in 25 ml boiling ether. It is cooled. It is filtrated and vacuum dried upon phosphorous pentoxyde. A white solid is obtained.

Mass of 1 R (+) compound: 5.31 g-Yield 87%. F: 69° C. (Kofler) $(\alpha)_D^{25} = +23.9°$, c=1.2 MeOH.

NMR $^1$H: 7.36 (s,5H); 7.24 (s,5H); 5.85 (s, 1H); 5.14 (s, 2H); 3.95 (dd, 2H, J1=3.3 Hz, J2=4.6 Hz); 3.22-2.74 (m, 5H); 2.34 (s, 3H). (CDCl$_3$, TMS).

IR (cm -1): 3280; 1755; 1695; 1640. (Nujol)

NMR $^{13}$C: 195.8 (s); 172.9 (s); 169.2 (s); 138.4 (s); 134.9 (s); 128.7 (d); 128.4 (d); 128.2 (d); 127.7 (d); 127.5 (d); 127.3 (d); 126.5 (d); 66.9 (t); 49.1 (d); 41.2 (t); 38.2 (t); 31.0 (t); 30.4 (q). (CDCl$_3$)

This compound, R(+), will hereafter be designated as compound (1).

Microanalysis:

| | C% | N% | H% |
|---|---|---|---|
| Found: | 65.34; | 3.95; | 6.10 |
| Calc.: | 65.45 | 3.63 | 5.97. |

EXAMPLE 2

N-/2-acetylthiomethyl-1-oxo-3-phenylpropyl/-glycine (S) (−) benzyl ester.

The method used in Example 1 is followed using (−) ephedrin. The characteristics of ephedrinium (−) 3-acetylthio-2-benzylpropionate are identical with those of its enantiomer described in Example 1, except for its rotatory power.

F=124°-126°, (Microscope) $(\alpha)_D^{25} = -49.3°$ (1.4 MeOH).

(−) 3-acetylthio-2-benzylpropanoic acid is freed under the same conditions as in Example 1.

$(\alpha)_D^{25} = -36.4°$ (1.3 MeOH).

For the synthesis of (S) acetorphan, the method described in Example 1 from S (−) acid is followed.

Yield 84%. $(\alpha)_D^{25} = -24.1°$, c=1.3, MeOH.

The spectral characteristics of Example 2 S (−) are the same as those of its enantiomer.

F: 71° C. (K). Microanalysis: Found: C % 65.02 N % 3.88 H % 5.87 Calc.: C % 65.45 N % 3.63 H % 5.97.

This compound will be hereafter be designated as compound (2).

In a variant compound (2) can also be prepared as an example starting from the filtrate obtained in Example 1 after extracting ephedrinium (+) 3-acetylthio-2-benzylpropionate. The filtrate is treated with (−) ephedrin, the treatment proceeding as in Example 2.

EXAMPLE 3

N-/2-acetylthiomethyl-1-oxo-3-phenylpropyl/glycine (R) methyl ester

Under the conditions described for Example 1, the R (+) acid is coupled with methyl glycinate and the expected product is obtained with a comparable yield. This compound will be hereafter designated as compound (3).

Yield 84% (silica gel chromatography) F: 76°-77° (Kofler) $(\alpha)_D^{25} = +29.6°$ (c=1.0; MeOH). IR (nujol) (cm$^{-1}$): 3300, 1755, 1690, 1660 $^1$H-NMR (CDCl3): 7.15 (s, 5H); 6.25(l, 1H, J=5.6 Hz); 3.9 (dd, 1H, J=5.6 Hz); 3.85 (dd, 1H, J=5.6 Hz); 3.6 (s, 3H); 3.2-2.5 (m, 5H), 2.2 (s, 3H). $^{13}$C-NMR (CDCl3): 196.0(s); 172.9(s); 169.7(s); 138.3(s); 128.6(d); 128.2(d); 126.3(d); 51.9(q); 48.6(d); 40.8(t); 38.0(t); 30.8(t); 30.3(q).

Microanalysis: Found: C % 58.32 N % 4.54 H % 6.14 Calc.: C % 58.25 N % 4.53 H % 6.14

EXAMPLE 4

N-/2-acetylthiomethyl-1-oxo-2-phenylpropyl/-glycine (S) methyl ester

The S (−) acid is coupled, under conditions which are described to obtain Example 2, with methyl glycinate. This compound will be hereafter designated as compound (4).

EXAMPLE 5

(R) N-/2-acetylthiomethyl-1-oxo-3-phenylpropyl/-(S)-alanine methyl ester

The R (+) acid is coupled, under conditions which are described to obtain Example 1, with (S) methyl alaninate. This compound will be hereafter designated as compound (5).

Yield 70% F=56° C. (Microscope) $(\alpha)_D^{25} = +9.1°$ (1.37, MeOH) IR: 3300, 1735, 1680, 1650 (nujol) $^1$H-NMR (CDCl3): 7.2 (s, 5H); 6.6 (m, 1H); 4.5 (m, 1H); 2.7-3.3(-m, 5H); 2.3 (s, 3H); 1.1 (d, J=7.3 Hz, 3H). $^{13}$C-NMR (CDCl3): 195.6 (s); 172.8 (s), 171.9 (s); 138.3 (s); 128.6 (d); 128.1 (d); 126.2 (d); 52.0 (q); 49.0 (d); 47.4 (d); 38.3 (t); 30.9 (t); 30.2 (q); 17.8 (q).

Microanalysis: Found: C % 59.7 N % 4.56 H % 6.66 Calc.: C % 59.42 N % 4.33 H % 6.54.

EXAMPLE 6

(S) N-/2-acetylthiomethyl-1-oxo-3-phenylpropyl/-(S) alanine methyl ester.

The S (−) acid is coupled under the conditions described to obtain Example 2 with (S) methyl alaninate. This compound will be hereafter designated as compound (6).

Yield 88%. F=83° C. (Microscope) $(\alpha)_D^{25} = -70.9°$ (1.3, MeOH) IR: 3300, 1755, 1695, 1650 (nujol) $^1$H-NMR (CDCl3): 7.2 (s, 5H); 6.6 (m, 1H); 4.5 (m, 1H); 2.7-3.3 (m, 5H); 2.3 (s, 3H); 1.33 (d, J=7.3 Hz, 3H).

Microanalysis: Found: C % 59.3 N % 4.42 H % 6.46 Calc.: C % 59.42 N % 4.33 H % 6.54.

BIOLOGICAL STUDY

Dosage of 'enkephalinase' activity and angiotensin convertase (ACE) activity with determination of the effect of inhibitors both in vitro and on mouses in vivo: inhibition of the same enzymes and protection of natriuretic auricular factor.

The results are given in the following Table.

ENKEPHALINASE AND ACE INHIBITING ACTIVITIES IN IN VITRO AND IN VIVO STRIATUM

TABLE 1

| | Enkephalinase | | ACE | |
|---|---|---|---|---|
| COMPOUNDS | In vitro(a) (IC50' nM) | In vivo(b) (DE50' mg/kg) | In vitro(c) (IC50' nM) | In vivo(d) (DE50' mg/kg) |
| (1) | 2 | 0.8 | 5,000 | inactive (>20) |
| (2) | 3 | 0.4 | 100 | 10 |
| (5) | 3 | 0.9 | 2,000 | (>20) inactive |
| (6) | 1.2 | 0.3 | 12 | 4 |

(a) Activity measured on striatum membranes according to Llorens et al., J. Neurochem., 1982, 39, 1081.
(b) Activity measured in mouse striatum 30 mn after i.v. administration according to Llorens-Cortes et al., Eur. J. Pharmacol., 1985, 119, 183.
(c) and (d) Activities measured on mouse striatum membranes in vitro or 30 mn after i.v. administration according to Yang and Neff, J. Neurochem., 1972, 19, 2443.

ENKEPHALINASE INHIBITING ACTIVITIES AND PROTECTION OF NATRIURETIC AURICULAR FACTOR (ANF) IN THE KIDNEY IN VIVO

TABLE 2

|  | Inhibition of enkephalinase (%) (a) | Increase of ANF (%) (b) |
| --- | --- | --- |
| COMPOUND (1) | 15 ± 6 | inactive |
| COMPOUND (2) | 54 ± 6 | 33 ± 3 |

(a)Inhibition of the linking between $^1$H Acetorphan and renal enkephalinase measured according to S. de la Baume, M. Tuong, F. Brion, J. C. Schwartz (J.P.E.T. 1988, forthcoming) 90 minutes after oral administration of compounds 1 or 2 at a dose of 0.3 mg/kg.
(b)Increase in the renal level of $^{125}$I ANF, as measured 2 min after i.v. administration of $10^6$ cpm to mouses having been given compounds 1 or 2, 90 min before (0.3 mg/kg, orally).

Compound 2 (0.3 mg/kg, p.o.) induces in the same test an increase of renal $^{125}$I ANF of 75±7% after 30 min and ±5% after 180 min.

PHARMACOLOGICAL STUDY

The pharmacological study of heretofore described products has allowed one to establish an antalgic, psychotropic, antidiarrheic, gastric antacid and anti-inflammatory effect in experimentally provoked cholecystitis.

The pharmacological tests which were undertaken were the following:

I. ACUTE TOXICITY

The determination of mortality among mouses is observed after a single intraveinous administration of increasing doses of compounds to be tested.

The LD50 for the compounds under study is above 100 mg/kg/i.v.

II. SUBACUTE TOXICITY

Compound (1) was administered during 3 weeks to mouses at an oral dose of 2 g/kg/day. No weight development change and no toxic signs were observed on the animals as opposed to control. Organ weight and pathological examination after the animals were killed show no difference as opposed to control.

Moreover, no signs of tolerance, habituation or other weaning phenomenon were observed on animals submitted to a reversibility test after treatment.

III. ANALGESIC ACTIVITIES MEASURED ON PLATE JUMP TEST AT 55° C. AFTER ADMINISTRATION TO MOUSES.

(Eddy and Leimbach, J. Pharmacol. Exp. Ther. 1953, 107 385).

TABLE 3

| Adm. time before test | Dose (mg/kg) | Route | Reaction time (sec) |
| --- | --- | --- | --- |
| Control |  |  | 50 ± 5 |
| Compound (1) | 1 h | 30 | oral | 80 ± 6* |
| Compound (1) | 1 h | 100 | oral | 140 ± 10* |
| Compound (2) | 1 h | 30 | oral | 75 ± 5* |
| Compound (1) | 20' | 5 | i.v. | 85 ± 5* |

*P < 0,01

The lack of ACE-inhibiting effect of compound 1 allows it to be administered at a high dose.

IV. ANTIDIARRHEIC ACTIVITY AS MEASURED ON RATS TREATED WITH CASTOR OIL (Neimegers et al., Arzneim. Forsch., 1974, 24, 1622).

TABLE 4

|  | Time before appearance of diarrheic stools (min) |
| --- | --- |
| Control | 80' ± 5 |
| Compound (1) (20 mg/kg, p.o.) | 190' ± 30* |
| Compound (2) (10 mg/kg, p.o.) | 160' ± 25* |

Inventive compounds (1) and (2) were administered 30 min before castor oil.
*p < 0.01

V. COLIC MOTIVE ACTIVITY

On dogs during postprandial periods compound (1) potentiates an increase in colic motricity as an answer to the intake of food.

TABLE 5

| Motive index (as evaluated with a restraint gauge). | | | | |
| --- | --- | --- | --- | --- |
|  |  | Before meal | After meal | |
| Route | Dose (mg/kg) | (−2/0) | (0/+2 h) | (+2/10 h) |
| Control | — | 6.1 ± 1.5 | 8.8 ± 1.9 | 11.2 ± 2.5 |
| Compound (1) i.v. | 1 | 5.9 ± 0.7 | 15.2 ± 2.4* | 18.3 ± 3.1* |
| Compound (1) p.o. | 10 | 6.4 ± 0.8 | 17.4 ± 2.7* | 21.5 ± 4.6* |
| Compound (2) p.o. | 5 | 6.2 ± 0.9 | 16.3 ± 2.5* | 20.1 ± 3.7* |

Influence of previous intraveinous (i.v.) or oral (p.o.) administration of coupound on the variations of the colic motive index after standard meal on dogs.
*p < 0.01.

VI. GASTRIC ACID ACTIVITY INHIBITING ACTION.

The stimulation of gastric acid secretion of cats induced by Pentagastrin, 2-deoxyglucose and histamin is significatively decreased (p<0.05) by the administration of compounds (1) and (2) at a dose of 0.5, 1.5 and 5 mg/kg i.v.

VII. ANTI-INFLAMMATORY ACTIVITY IN EXPERIMENTAL CHOLECYSTITIS.

Given to cats (Method according to SVAVIK J. et al., SURGERY, 1981, 90, 500) at a dose of 3 mg/kg i.v. compound (1) significantly decreases hypersecretion as induced by an inflammation of the gall bladder.

TABLE 6

| Compounds | Net water secretion (ml/h) of animals with cholecystitis (n = 10) |
| --- | --- |
| Control | 0,85 ± 0.23 |
| Compound (1) | 0,21 ± 0.15* |

*p < 0,05

CLINICAL PHARMACOLOGY STUDY

With healthy volunteers (9 male subjects) enkephalinase and natriuretic auricular factor (ANF) plasma levels as well as diuresis and natruresis are measured after oral administration of either a placebo, or (S) acetorphan.

As opposed to the placebo sequence, plasma enkephalinase is significantly inhibited (p<0.001) by 62% and plasma ANF is increased by 50% (p<0.05) 1 hr after administration of 30 mg (S) acetorphan, whereas diuresis and natriuresis increase respectively by 42% and 46% (p<0.05) between 2 and 8 hours after administration of the product.

The results of these studies establish the weak toxicity and interesting inhibiting properties of enkephalinase, notably as antalgic, psychotropic, antidiarrheic regulating colic motricity, anti-gastric acid and anti-inflammatory agents during experimental cholecystites of the inventive compounds; the protecting effect of natriuretic auricular factor (ANF) entails a useful diuretic and natruretic activity during cardiac and hepatorenal insufficiency as well as high blood pressure.

These properties make them useful in human and veterinary medicine. Compounds (1), (3) and (5), (R), are useful both for central and peripheral indications, notably as antalgic and psychotropic agents and as drugs for curing functional colopathy (irritable bowel syndrone), gastro-oesophageal regurgitation and acute cholecystitis. They can be administered even at high unit doses, preferably 50 to 500 mg active principle and with a daily posology preferably between 50 mg and 1 g active principle.

Compounds (2), (4) and (6), i.e. (S), will be preferably useful for peripheral indications: functional colopathy, gastro-oesophageal regurgitation and acute cholecystitis, and above all for cardiovascular indications for which advantage is taken of the important protecting effect of ANF for the treatment of cardiac and hepatorenal insufficiency and high blood pressure at weak unit doses, preferably 5-100 mg active principle, with daily posologies varying between preferably 5 and 200 mg active principle.

The inventive drugs can be administered to man by oral, parenteral or rectal routes.

We claim:

1. An enantiomer (S) compound having the formula

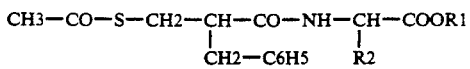

in which

R1 = CH3 or CH2—C6H5    R2 = H.

2. An enantiomer (S) compound according to claim 1, having the formula

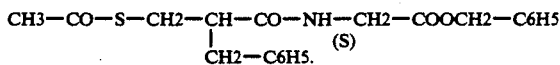

3. A drug according to claim 1, characterized by a unit dose of 5-100 mg active principle, the doses to be administered daily being between 5 and 200 mg.

4. A drug composition having natriuretic auricular factor protection, diuretic and natriuretic activities, characterized in that it contains, as an active ingredient, an effective amount of a S(−) compound according to one of claims 1 or 2.

5. A drug composition for treatment of high blood pressure, cardiac insufficiency, or hepatorenal insufficiency, characterized in that it contains, as an active principle, a S(−) compound, of claim 2.

6. A drug composition for treatment of high blood pressure, cardiac insufficiency or hepatornal insufficiency, characterized in that it contains, as an active ingredient, a S(−) compound, of claim 2.

* * * * *